(12) United States Patent
R. Marcelo et al.

(10) Patent No.: US 8,975,466 B2
(45) Date of Patent: *Mar. 10, 2015

(54) ABSORBENT ARTICLE INCLUDING A PLURALITY OF LONGITUDINALLY EXTENDING CHANNELS

(75) Inventors: Ana Maria Elena R. Marcelo, Maplewoods (SG); Fernanda Wiermann Paques, Sao Jose dos Campos (BR); Steven H. White, Flemington, NJ (US)

(73) Assignee: Eveready Battery Company, Inc., St. Louis, MO (US)

( * ) Notice: Subject to any disclaimer, the term of this patent is extended or adjusted under 35 U.S.C. 154(b) by 120 days.

This patent is subject to a terminal disclaimer.

(21) Appl. No.: 13/205,790

(22) Filed: Aug. 9, 2011

(65) Prior Publication Data

US 2012/0004633 A1 Jan. 5, 2012

Related U.S. Application Data

(63) Continuation-in-part of application No. 12/431,793, filed on Apr. 29, 2009, now Pat. No. 8,034,991.

(51) Int. Cl.
| | |
|---|---|
| *A61F 13/15* | (2006.01) |
| *A61F 13/20* | (2006.01) |
| *A61F 13/475* | (2006.01) |
| *A61F 13/537* | (2006.01) |

(52) U.S. Cl.
CPC ......... *A61F 13/4758* (2013.01); *A61F 13/4756* (2013.01); *A61F 13/53713* (2013.01); *A61F 2013/53726* (2013.01); *A61F 2013/53782* (2013.01)
USPC ............................. 604/380; 604/378; 604/379

(58) Field of Classification Search
CPC ................... A61F 13/4756; A61F 2013/53734
USPC ......................... 604/378, 380; D24/124–126
See application file for complete search history.

(56) References Cited

U.S. PATENT DOCUMENTS

| | | | | |
|---|---|---|---|---|
| 4,059,114 | A | * | 11/1977 | Richards ....................... 604/359 |
| 4,623,340 | A | | 11/1986 | Luceri |
| D508,993 | S | * | 8/2005 | Drzewiecki et al. ......... D24/125 |
| 7,223,900 | B1 | | 5/2007 | Lariviere et al. |

(Continued)

FOREIGN PATENT DOCUMENTS

| | | |
|---|---|---|
| CN | 101347370 A | 1/2009 |
| EP | 0613671 A2 | 9/1994 |

OTHER PUBLICATIONS

European Search Report dated Oct. 31, 2012 for corresponding EPA No. 12179695.7.

(Continued)

*Primary Examiner* — Melanie Hand
*Assistant Examiner* — Aundria Hairell
(74) *Attorney, Agent, or Firm* — Energizer Personal Care, LLC

(57) ABSTRACT

An absorbent article including a first end region, a second end region and a central region, a plurality of channels arranged in each of the first and second end regions, at least one channel arranged in the central region and extending in a longitudinal direction of the article, the at least one channel being connected at each end thereof to the plurality of channels in the first end region and the plurality of channels in the second end region.

20 Claims, 9 Drawing Sheets

(56) References Cited

U.S. PATENT DOCUMENTS

2003/0135182 A1* 7/2003 Woon et al. .................. 604/378
2007/0219515 A1* 9/2007 Marsh et al. ................. 604/359

OTHER PUBLICATIONS

European Search Report dated Nov. 6, 2012 for corresponding EPA No. 10250852.0.

* cited by examiner

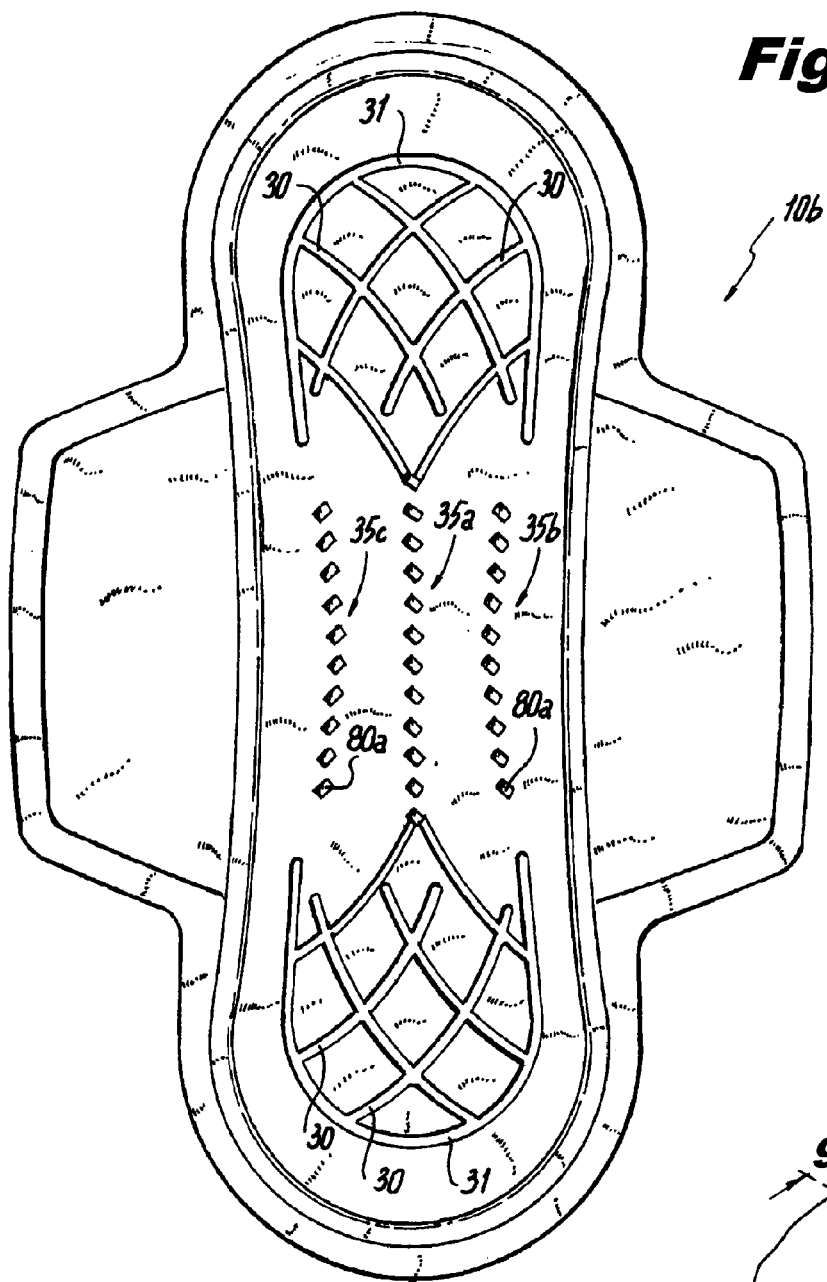
Fig. 7
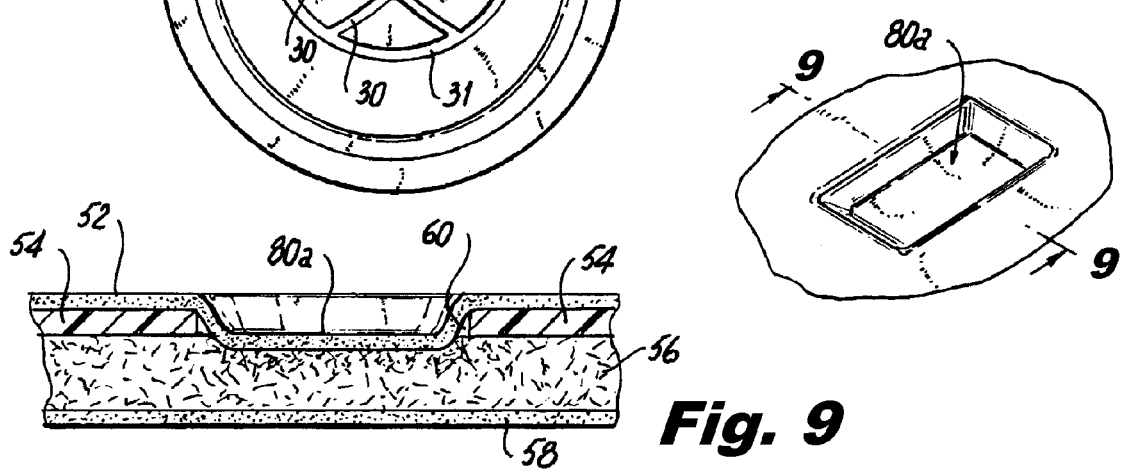
Fig. 8
Fig. 9

ABSORBENT ARTICLE INCLUDING A PLURALITY OF LONGITUDINALLY EXTENDING CHANNELS

CROSS REFERENCE TO RELATED APPLICATION

The present application is a continuation-in-part application of U.S. patent application Ser. No. 12/431,793 filed on Apr. 29, 2009 now U.S. Pat. No. 8,034,991, priority of which is hereby claimed.

FIELD OF INVENTION

The present invention generally relates to absorbent sanitary napkins and in particular to a sanitary napkin including a plurality of longitudinally extending channels for promoting enhanced fluid wicking in the longitudinal direction of the napkin.

BACKGROUND OF THE INVENTION

In order for a sanitary napkin to efficiently absorb a large amount of fluid during use it must effectively wick fluid throughout the absorbent structure of the napkin. Absent effective wicking properties menstrual fluid tends to pool in certain regions of the napkin as a result of which the full absorbent capacity of the napkin is not effectively utilized. In addition to having superior wicking capabilities, sanitary napkins must also be able to quickly absorb fluid. That is, sanitary napkins must also have superior fluid penetration characteristics. Accordingly, the inventors of the present invention have recognized a need to provide a sanitary napkin that efficiently wicks fluid in the longitudinal direction of the napkin while at the same time providing superior fluid penetration characteristics. By providing a napkin that efficiently wicks fluid in the longitudinal direction, while at the same time quickly absorbs fluid, the inventors have provided a sanitary napkin that exhibits superior fluid handling characteristics and effectively utilizes the full absorbent capacity of the napkin.

SUMMARY OF THE INVENTION

In view of the foregoing, the present invention provides an absorbent article including a longitudinally extending centerline, a transversely extending centerline, a first end region and a second end region, a central region arranged between the first and second end regions, a first longitudinal edge, a second longitudinal edge, a first transverse edge, a second transverse edge, a main absorbent body, a first embossing pattern having a first portion arranged in the first end region and a second portion arranged in the second end region, each of the first and second portions including a plurality of interconnected channels, the interconnected channels defining a plurality of body facing protrusions, and a second embossing pattern including at least one channel arranged in the central region and extending in a longitudinal direction of the article, the at least one channel intersecting at least one of the plurality of interconnected channels in the first end region and at least one of the plurality of interconnected channels in the second end region.

BRIEF DESCRIPTION OF THE DRAWINGS

Examples of embodiments of the present invention will now be described with reference to the drawings, in which:

FIG. 7 is a top plan view of an absorbent article according to a third embodiment of the present invention;

FIG. 8 is a detailed perspective view of a portion of the absorbent article shown in FIG. 7;

FIG. 9 is a sectional view taken along line 9-9 in FIG. 8;

DETAILED DESCRIPTION OF THE INVENTION

The present invention generally relates to disposable absorbent articles such as sanitary napkins, pantiliners, absorbent products for incontinence, and other disposable absorbent articles worn close to a wearer's body. Although the invention will be described herein with reference to a sanitary napkin, the invention may be utilized with other disposable absorbent articles.

Absorbent articles according to the present invention provide superior fluid handling characteristics, and more specifically provide superior longitudinal wicking characteristics. In addition, absorbent articles according to the present invention provide superior fluid penetration characteristics.

Figure 1:
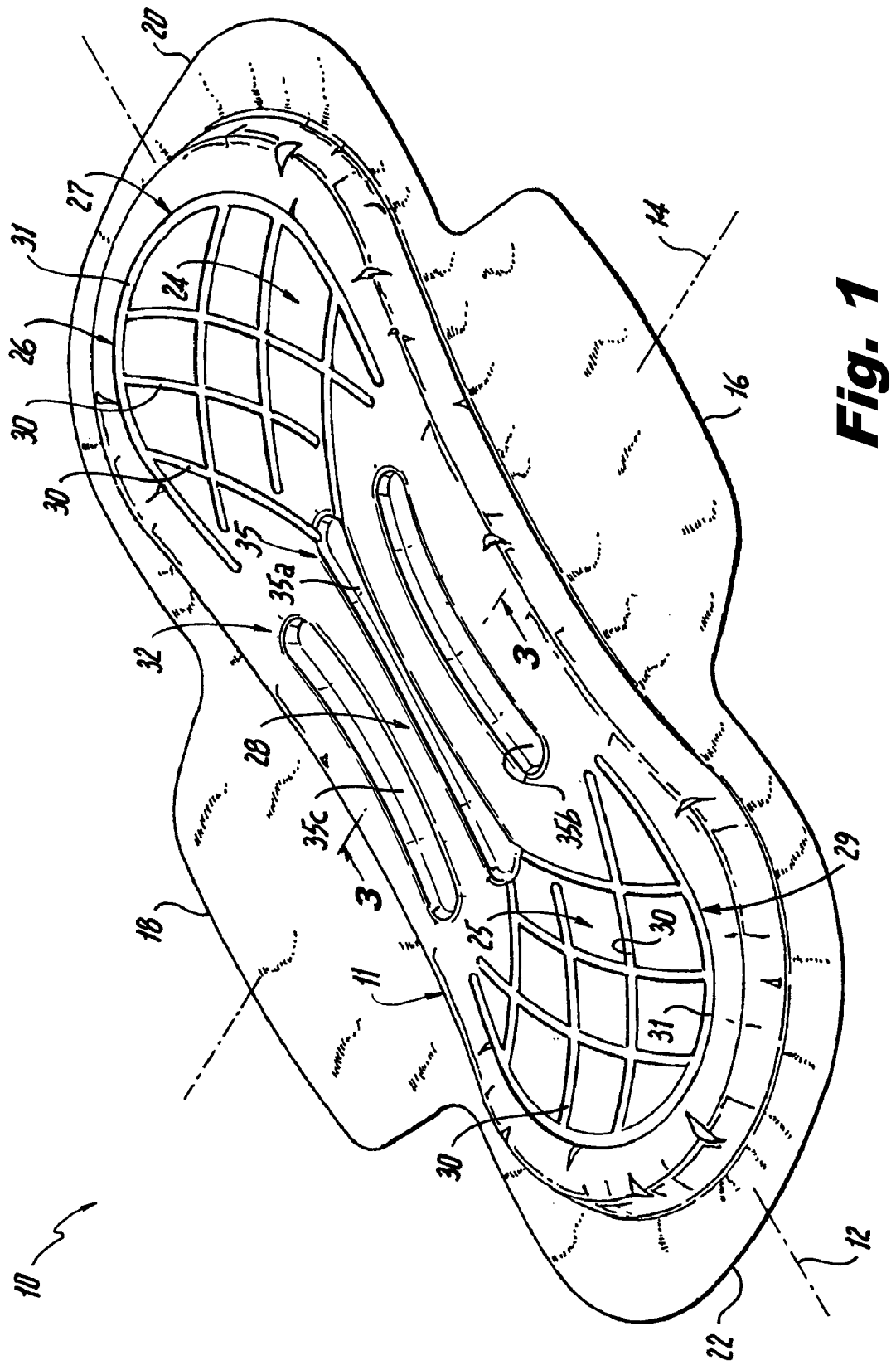
FIG. 1 is a perspective view of an absorbent article according to a first embodiment of the present invention.

A specific embodiment of a sanitary napkin 10 according to the present invention is illustrated in FIG. 1. The sanitary napkin 10 includes a main absorbent body 11, a longitudinally extending centerline 12, a transversely extending centerline 14, a first longitudinal edge 16, a second longitudinal edge 18, a first transverse edge 20, a second transverse edge 22, a first end region 24, a second end region 25, and a central region 28 located between the first end second end regions, 24 and 25. The term "main absorbent body" as used herein means the area defined by primary absorbent portions of the napkin excluding any area defined solely by the cover and/or barrier, and excluding any area defined by the wings of the product.

The napkin 10 further includes a first embossing pattern 26. The first embossing pattern 26 has a first portion 27 arranged in the first end region 24 and a second portion 29 located in the second end region 25, thus the first and second portions 27 and 29 are spaced from one another in the longitudinal direction of the napkin 10. Each of the first portion 27 and second portion 29 comprise a plurality of interconnected arcuate channels 30, each one of the channels 30 extending from one side of the napkin, across the longitudinally extending centerline 12, to the other side of the napkin. Each one of the channels 30 intersects at least one other channel 30 at an oblique angle relative thereto and each one of the channels 30 extends across the longitudinally extending centerline 12 at an oblique angle relative thereto. Each of the first and second portions 27 and 29 further include a substantially U-shaped end channel 31. Each of the channels 30, at a distal portion thereof (i.e. that portion of the channel 30 located furthest from the intersection of the longitudinally extending centerline 12 and transversely extending centerline 14), intersect with, and terminate at, the end channel 31.

Each of the channels 30 is substantially arcuate in shape and has a length in the range of about 2 cm to about 10 cm, more preferably from about 5.0 cm to about 8.0 cm, when measured along the path of the channel 30. Each of the channels 30 has a width in the range of from about 1 mm to about 10 mm, more preferably from about 2 mm to about 4.0 mm. Each of the channels 30 has a depth of about 0.5 mm to about 5 mm, more preferably about 1 mm to about 3 mm, when measured from a top surface of the napkin 10. Each end channel 31 has a length in the range of about 5 cm to about 25 cm, more preferably from about 10 cm to about 15 cm. Each end channel 31 has a depth of about 0.5 mm to about 5 mm, more preferably about 1 mm to about 3 mm, when measured from a top surface of the napkin 10.

The channels 30 function to transport fluid towards the ends regions 24, 25 of the napkin 10 to thereby utilize the full absorbent capacity of the article along its length. The end channels 31 function to prevent fluid from being transported to the very end the napkin and in this manner serve to prevent end leakage, that is the leakage of fluid beyond the transverse edges 20 and 22 of the napkin. In this regard, each of the channels 31 are preferably spaced from a respective transverse edge, 20 and 22, of the napkin by a distance of from about 5 mm to about 30 mm, more preferably from about 10 mm to about 20 mm.

The napkin 10 further includes a second embossing pattern 32. The second embossing pattern 32 is generally located in the central region 28 of the napkin 10. The second embossing pattern 32 includes at least one longitudinally extending channel 35. Absorbent articles according to the present invention preferably have between about 1 and about 5 channels 35. In the specific embodiment shown in FIG. 1, the second embossing pattern 32 includes three generally longitudinally extending channels 35a, 35b and 35c. The longitudinally extending channel 35a is coextensive with the longitudinally extending centerline 12 and arranged symmetrically with respect thereto. Each of the channels 35b and 35c are arranged in spaced relationship to channel 35a and generally have an arcuate shape. In addition, channels 35b and 35c are symmetrically arranged relative to the longitudinally extending centerline 12 and are shaped such that they are concave relative to the longitudinally extending centerline 12. Each one of the channels, 35a, 35b, and 35c preferably has a length in the range of about 3 cm to about 15 cm, more preferably from about 4.5 cm to about 10 cm, when measured along a path of the channel. Each of the channels, 35a, 35b and 35c preferably has a width in the range of from about 1 mm to about 20 mm, more preferably from about 2 mm to about 10 mm. Each of the channels 35a, 35b and 35c preferably has a depth in the range of from about 1 mm to about 10 mm, more preferably between about 2 mm and about 5 mm.

Preferably, at least one of the channels 35a, 35b, and 35c intersects at least one of the channels 30 in the first end region 24 and at least one of the channels 30 in the second end region 25. In the specific embodiment of the invention shown in FIG. 1, channel 35a intersects, at respective ends thereof, a channel 30 in the first end region 24 and another channel 30 located in the second end region 25. The interconnection of channel 35a with the first 27 and second 29 portions of the first embossing pattern 26 enable the sanitary napkin 10 to effectively wick fluid from the central region 28 of the napkin 10 to the end regions 24 and 25 of the napkin. In this manner, the full absorbent capacity of the napkin 10 is utilized.

Figures 2, 3:
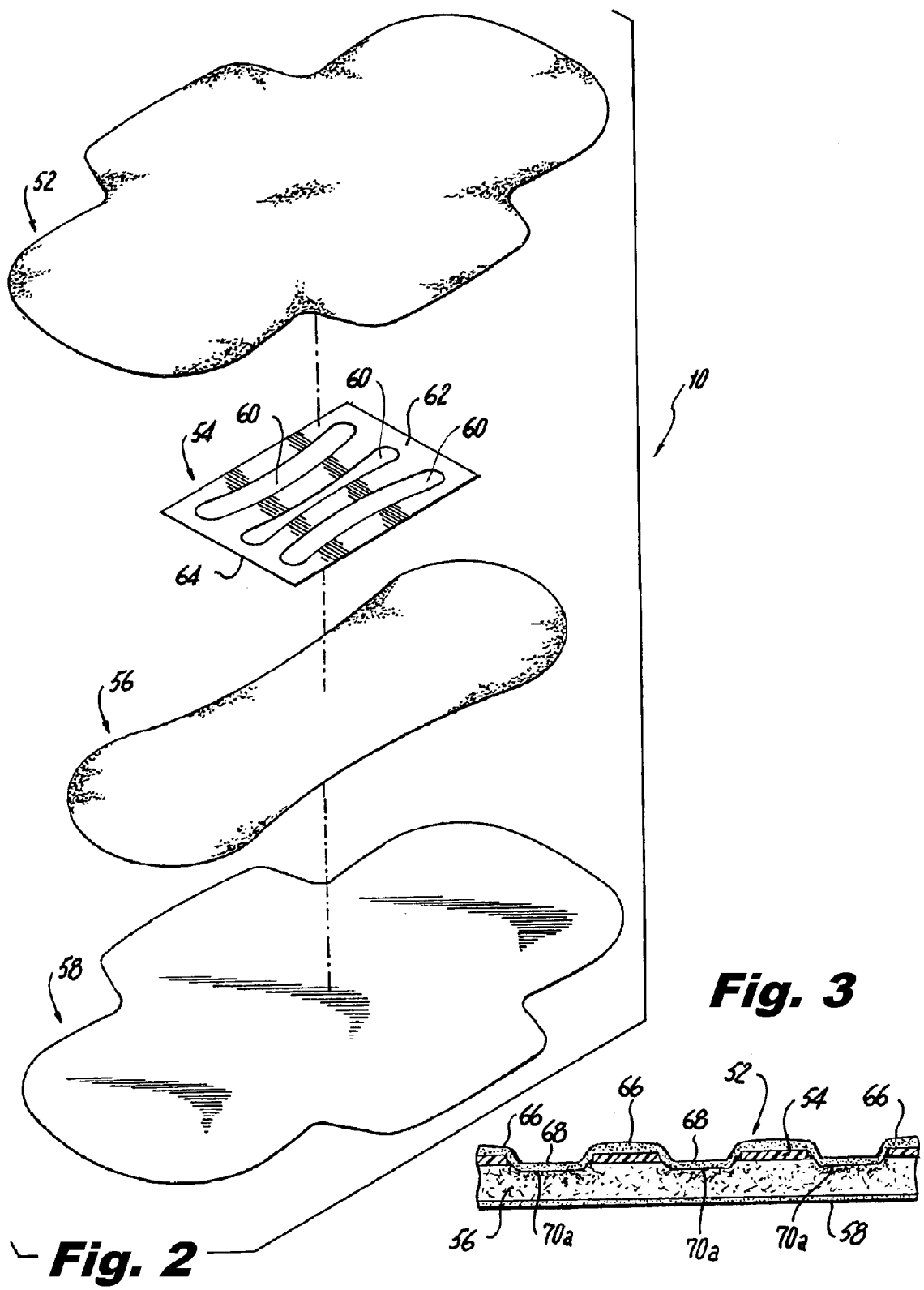
FIG. 2 is an exploded view of the absorbent article shown in FIG. 1 depicting the constituent material layers thereof prior to embossing.
FIG. 3 is a sectional view taken along line 3-3 in FIG. 1.

In one embodiment of the invention, as best seen in the exploded view shown in FIG. 2, the sanitary napkin 10 includes a fluid permeable cover layer 52, a first absorbent layer 54, a second absorbent layer 56, and a fluid impermeable barrier layer 58. The first absorbent layer 54 includes a plurality of longitudinally extending material-free zones 60 that extend from an upper surface 62 of the first absorbent layer 54 to a lower surface 64 of the first absorbent layer 54. Each of the material-free zones 60 preferably has a length of from about 3 cm to about 15 cm, more preferably from about 4.5 cm to about 10 cm, when measured along a path of the material-free zone 60. Each of the material-free zones 60 preferably has a width in the range of from about 1 mm to about 20 mm, more preferably from about 2 mm to about 10 mm. It is noted that each of the material-free zones corresponds in size, shape and location to channels 35a, 35b, and 35c.

Absorbent articles according to the present invention preferably have between about 1 and about 5 longitudinally extending the material-free zones 60. Each of the material-free zones 60 is spaced from an adjacent material-free zone 60 in the transverse direction by a distance from about 0.5 cm to about 3 cm. The material-free zones 60 preferably extend over a surface area in the range of between 50 mm$^2$ and about 4000 mm$^2$.

As best seen in FIG. 3, the cover layer 52 includes a plurality of first regions 66 that are arranged in spaced relationship to the second absorbent layer 56 and a plurality of second regions 68 that are arranged in surface to surface contact with the second absorbent layer 56. This structure is formed during manufacture of the sanitary napkin 10 by utilizing an embossing roll having a surface pattern corresponding in size and shape to channels 35a, 35b, and 35c. Specifically, the cover 52 is embossed such that the regions 68 of the cover 52 are arranged in surface to surface contact with the second absorbent layer 56. Further, also during the embossing process, the second absorbent layer 56 is embossed to form channels 70a, 70b and 70c in the second absorbent layer 56 that correspond in shape and location to the channels 35a, 35b, and 35c. Of course, the embossing roll used during manufacture should also have surface features used to form the first embossing pattern 26.

The arrangement of the regions 68 in surface to surface contact with the second absorbent layer 56 permits the sanitary napkin 10 according to the present invention to quickly absorb fluid in the center of the napkin where such "gush management" is required. Also, the regions 66 of the cover, in cooperation with the channels 35a, 35b and 35c, permit the effective wicking of fluid to the end regions 24 and 25 of the napkin. In this manner, the sanitary napkin 10 according to the present invention can provide effective "gush management" while at the same time effectively utilizing the full absorbent capacity of the napkin 10 along its length.

Figure 4:
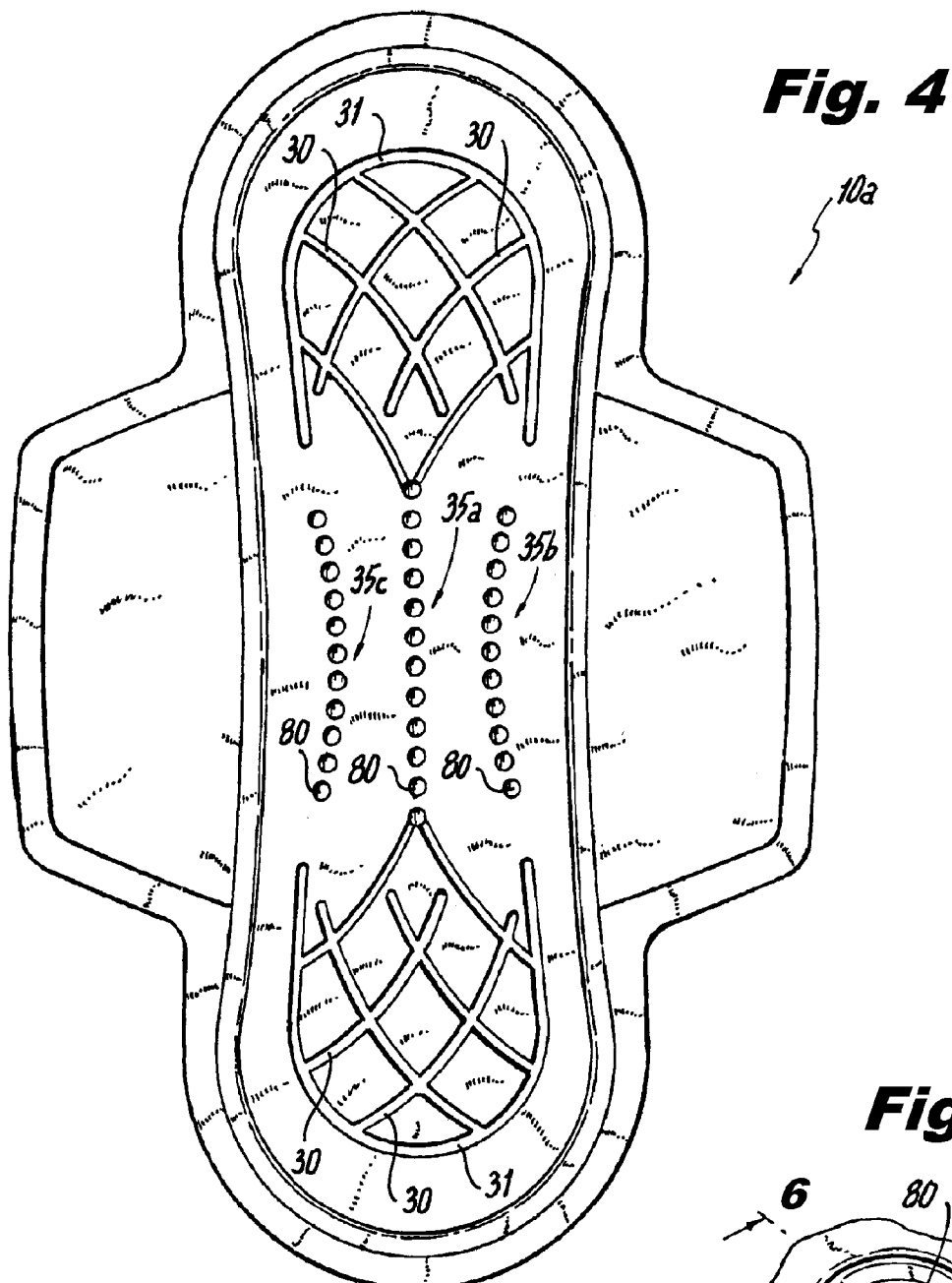
FIG. 4 is a top plan view of an absorbent article according to a second embodiment of the present invention.
Figure 6:
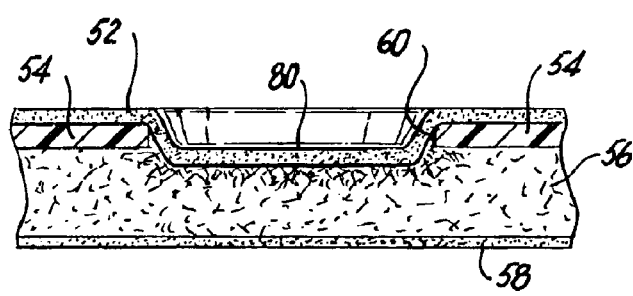
FIG. 6 is a sectional view taken along line 6-6 in FIG. 5.
Figure 5:
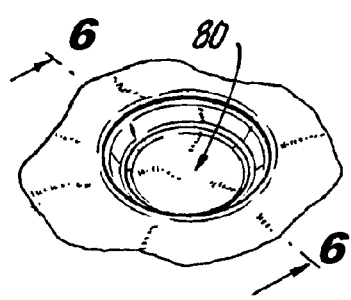
FIG. 5 is a detailed perspective view of a portion of the absorbent article shown in FIG. 4.

A sanitary napkin 10a, according to second embodiment of the present invention, is depicted in FIGS. 4-6. The sanitary napkin 10a has substantially the same structure, as sanitary napkin 10 described above. However, in the embodiment of the invention shown in FIGS. 4-6 the "channels" 35a, 35b and 35c are not continuous, as in napkin 10 described above, but rather are formed from a plurality of discretely arranged depressed regions 80. As shown in FIG. 4, each depressed region 80 is arranged in spaced relationship to an adjacent depressed region 80. The depressed regions 80 collectively cooperate to define "interrupted" channels 35a, 35b and 35c. In the particular embodiment of the invention shown in FIGS. 4-6 each depressed region 80 is circular in shape, as shown in detail in FIG. 5. In the embodiment shown in FIGS. 4-6, the first absorbent layer 54 includes a plurality of material-free zones 60 that each correspond in shape, size and location to a corresponding depressed region 80, one of such material-free zones 60 and corresponding depressed regions 80 being depicted in detail in FIG. 6.

A sanitary napkin 10b, according to third embodiment of the present invention, is depicted in FIGS. 7-9. The sanitary napkin 10b has substantially the same structure, as sanitary napkin 10a described above with reference to FIGS. 4-6. However, in the embodiment of the invention depicted in FIGS. 7-9 each depressed region 80a is rectangular or diamond in shape, as shown in detail in FIG. 8.

Figure 10:
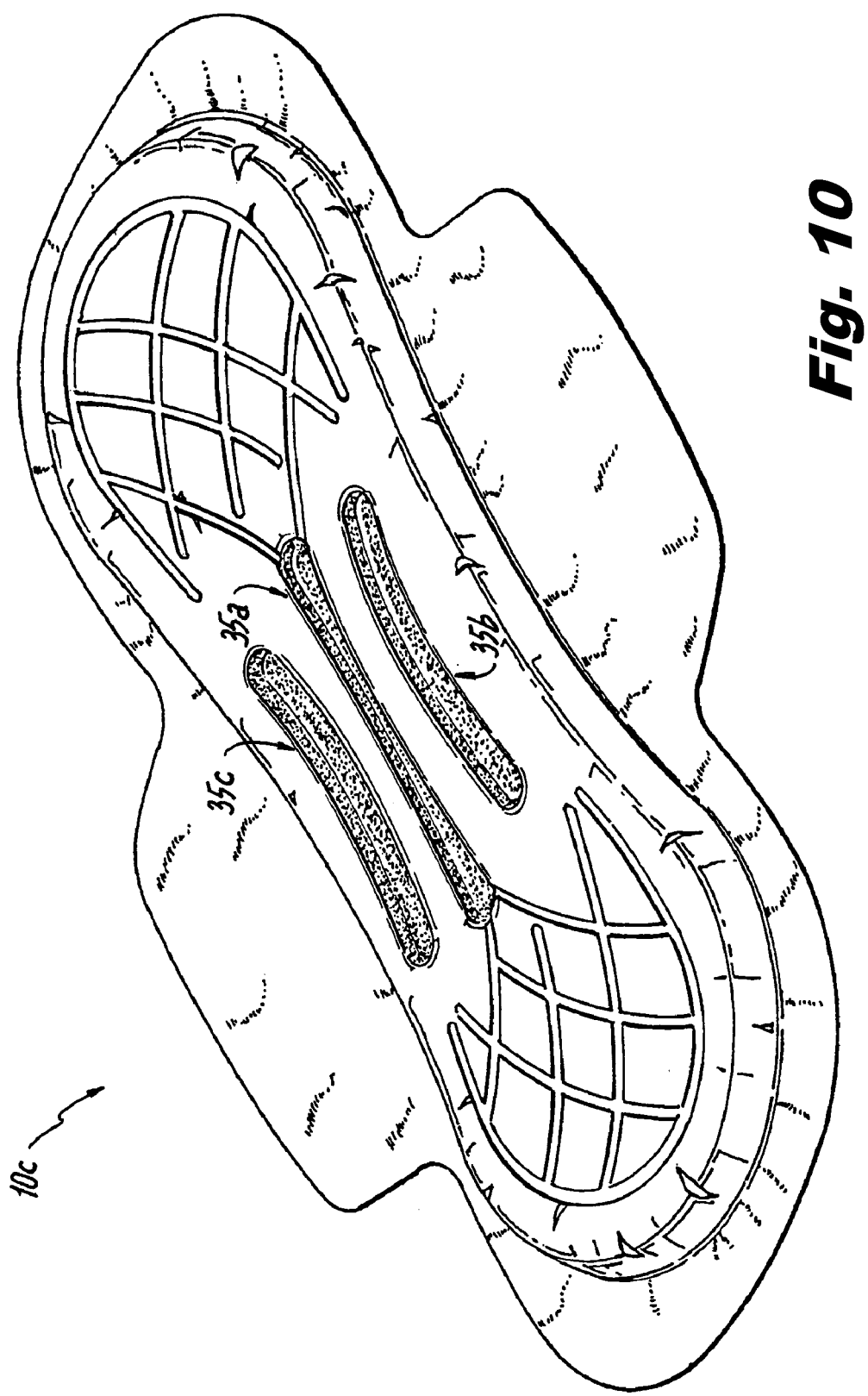
FIG. 10 is a perspective view of an absorbent article according to a fourth embodiment of the present invention.
Figure 11:
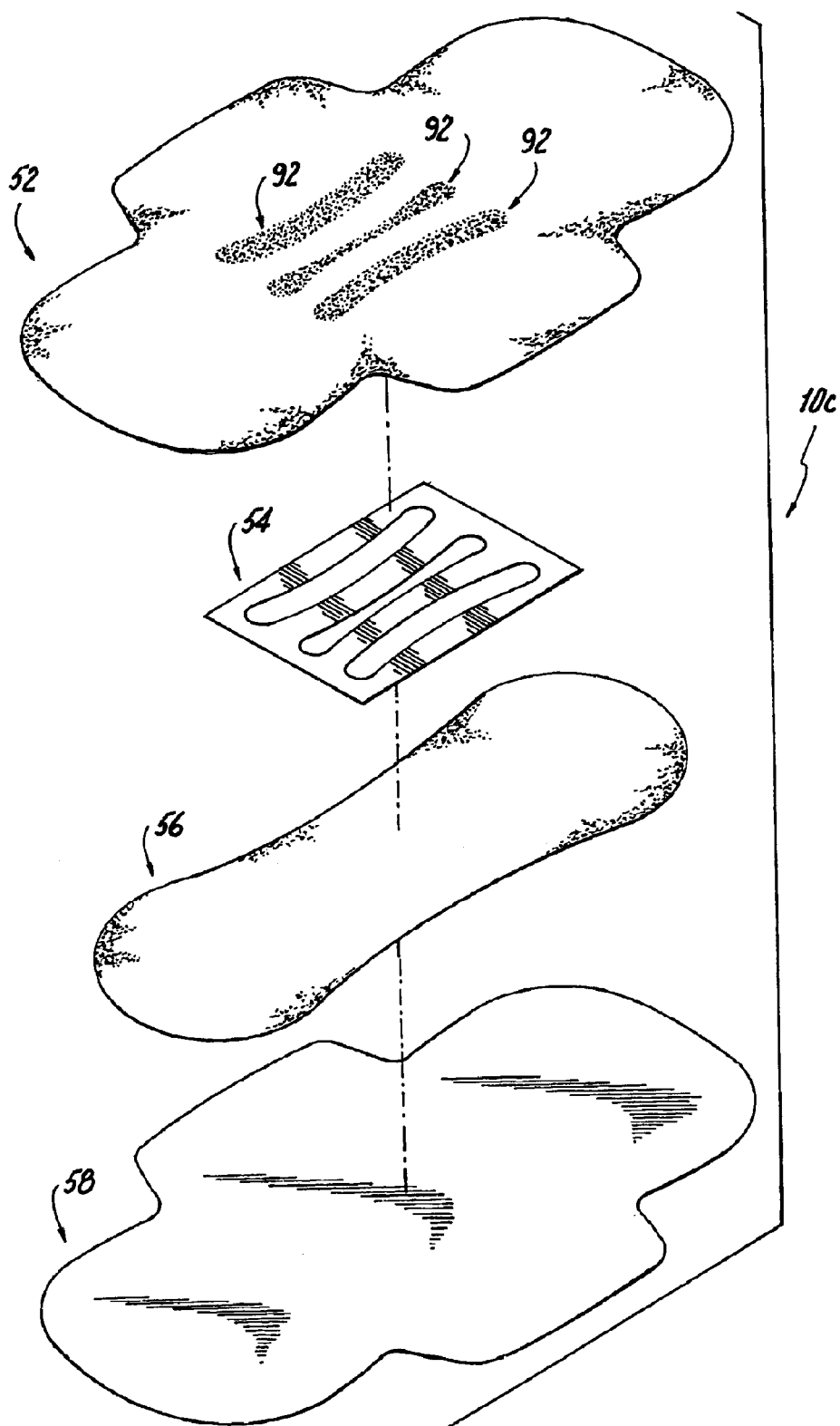
FIG. 11 is an exploded view of the absorbent article shown in FIG. 10, depicting the constituent material layers thereof prior to embossing.

A sanitary napkin 10c, according to a fourth embodiment of the present invention, is depicted in FIGS. 10-11. The sanitary napkin 10c has substantially an identical structure to sanitary napkin 10 described above. However, as shown in FIG. 10, the channels 35a, 35b and 35c are provided with color, to thereby provide a color cue that is visible to a user from a top surface of the napkin 10c. As shown in FIG. 11, the color cue may be provided by printing colored regions 92 on the cover layer 52. The colored regions 92 preferably correspond in size, shape and location to the channels 35a, 35b, and 35c. The colored regions 92 function provide the user with a color cue to the presence and function of the channels 35a, 35b and 35c. The colored regions 92 could alternatively be printed on the second absorbent layer 56 provided that such colored regions 92 can be viewed through the cover 52. Any means known to those of skill in the art may be utilized to provide the colored regions 92 such as printing, utilizing colored fibers, or any other suitable means.

A sanitary napkin 10d, according to a fifth embodiment of the present invention is illustrated in FIGS. 12-15. The sanitary napkin 10d includes a main absorbent body 11, a longitudinally extending centerline 12, a transversely extending centerline 14, a first longitudinal edge 16, a second longitudinal edge 18, a first transverse edge 20, a second transverse edge 22, a first end region 24, a second end region 25, and a central region 28 located between the first end second end regions, 24 and 25.

Figure 12:
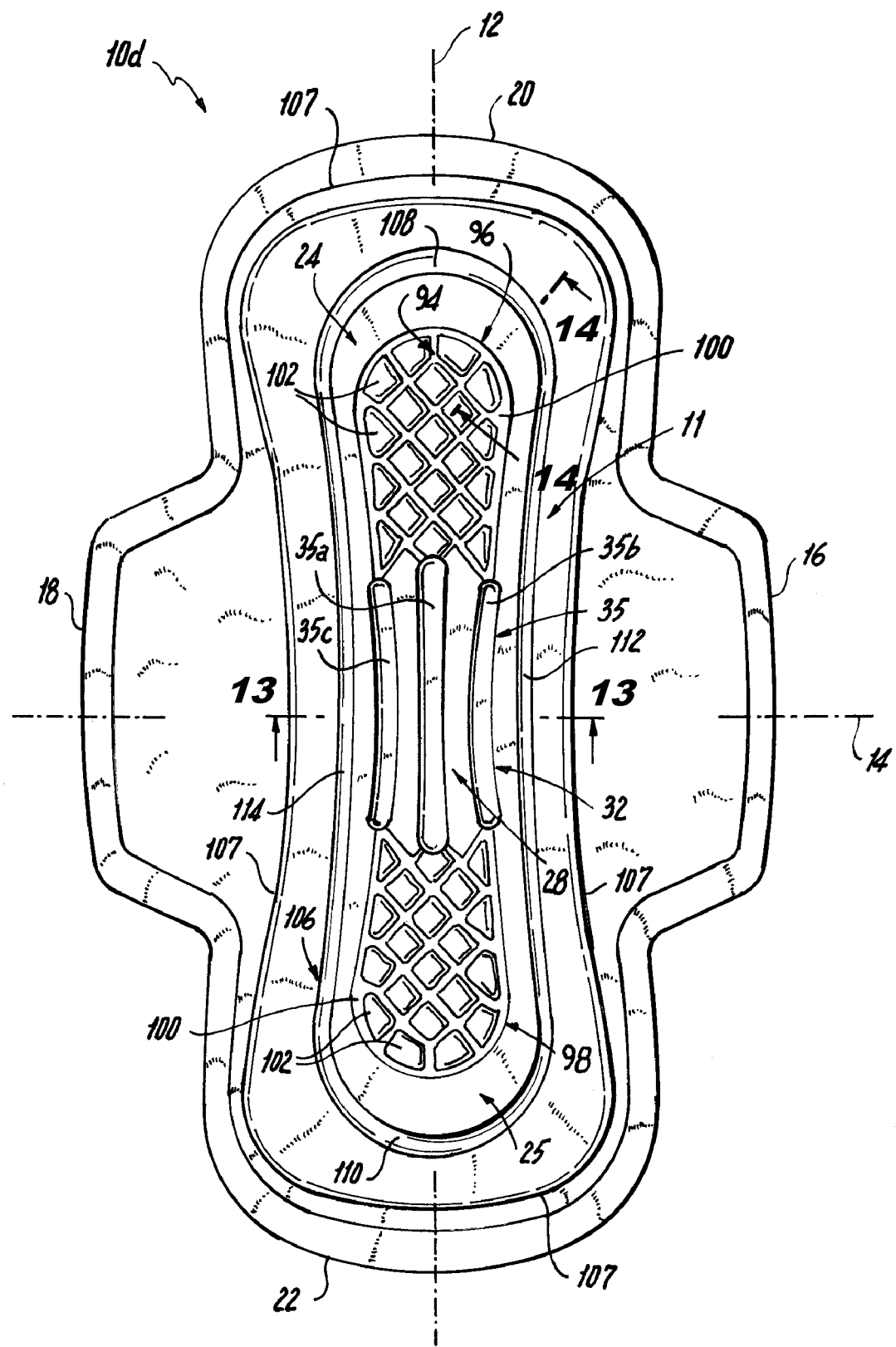
FIG. 12 is top plan view of an absorbent article according to a fifth embodiment of the present invention.
Figure 14:
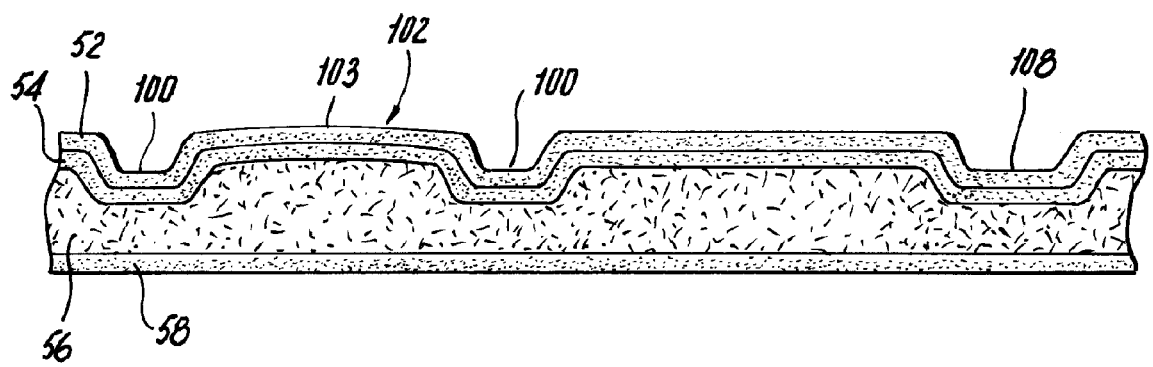
FIG. 14 is a sectional view of the absorbent article shown in FIG. 12 taken along line 14-14 thereof.

The napkin 10d further includes a first embossing pattern 94. The first embossing pattern 94 has a first portion 96 arranged in the first end region 24 and a second portion 98 located in the second end region 25, thus the first and second portions 27 and 29 are spaced from one another in the longitudinal direction of the napkin 10d. Each of the first portion 96 and second portion 98 comprise a plurality of interconnected channels 100. As shown in FIGS. 12 and 14, the interconnected channels 100 define therebetween a plurality of protrusions 102. When the napkin 10d is worn the protrusions 102 are positioned proximate (or in contact with) and facing the wearer's body. Each of the channels 100 preferably has a depth in the range of from about 1 mm to about 10 mm. Accordingly, an apex 103 (as best seen in FIG. 14) of each protrusion preferably extends from about 1 mm to about 10 mm above a base surface 104 of the surrounding channel 100.

As shown in FIG. 12 each protrusion 102 is substantially entirely surrounded by at least one of the channels 100. The channels 100 that surround each protrusion 102 are generally regions of reduced thickness or higher density than the protrusion 102 that is surrounded. Preferably, the channels 100 are connected to form a continuous network of interconnected channels 100.

The napkin 10d further includes a second embossing pattern 32. The second embossing pattern 32 is generally located in the central region 28 of the napkin 10d. The second embossing pattern 32 includes at least one longitudinally extending channel 35. Absorbent articles according to the present invention preferably have between about 1 and about 5 channels 35. In the specific embodiment shown in FIG. 12, the second embossing pattern 32 includes three generally longitudinally extending channels 35a, 35b and 35c. The longitudinally extending channel 35a is coextensive with the longitudinally extending centerline 12 and arranged symmetrically with respect thereto. Each of the channels 35b and 35c are arranged in spaced relationship to channel 35a and generally have an arcuate shape. In addition, channels 35b and 35c are symmetrically arranged relative to the longitudinally extending centerline 12 and are shaped such that they are concave relative to the longitudinally extending centerline 12. Each one of the channels, 35a, 35b, and 35c preferably has a length in the range of about 3 cm to about 15 cm, more preferably from about 4.5 cm to about 10 cm, when measured along a path of the channel. Each of the channels, 35a, 35b and 35c preferably has a width in the range of from about 1 mm to about 20 mm, more preferably from about 2 mm to about 10 mm. Each of the channels 35a, 35b and 35c preferably has a depth in the range of from about 1 mm to about 10 mm.

Preferably, at least one of the channels 35a, 35b, and 35c intersects at least one of the channels 100 in the first end region 24 and at least one of the channels 100 in the second end region 25. In the specific embodiment of the invention shown in FIG. 12, channel 35a intersects, at respective ends thereof, a channel 100 in the first end region 24 and another channel 100 located in the second end region 25. The interconnection of channel 35a with the first 27 and second 29 portions of the first embossing pattern 26 enable the sanitary napkin 10d to effectively wick fluid from the central region 28 of the napkin 10 to the end regions 24 and 25 of the napkin. In this manner, the full absorbent capacity of the napkin 10d is utilized.

As shown in FIG. 12, the sanitary napkin 10d further includes an embossed ring 106. The embossed ring 106 functions to stop fluid flow outside the area enclosed by the ring and thus helps prevent side and end leakage. The embossed ring 106 preferably has a width in the range of about 1 mm to about 10 mm, and a depth in the range of about 1 mm to about 10 mm. In the particular embodiment shown in FIG. 12, the embossed ring 106 is spaced outwardly relative to the first embossing pattern 94 and the second embossing pattern 32. Preferably the embossed ring is spaced outwardly from the first 94 and second 32 embossing patterns by a distance from about 2 mm to about 30 mm. In the particular embodiment of the invention shown in FIG. 12, the longitudinal end regions 108 and 110 of the embossed ring 106 are spaced further from the first 94 and second 32 embossing patterns than the side regions 112 and 114 of the embossed ring 106.

Preferably, the embossed ring is 106 is continuous, i.e. is not interrupted along its length, and completely surrounds the first embossing pattern 94 and second embossing pattern 32. In the particular embodiment of the invention shown in FIG. 12, the embossed ring 106 is arranged such that it is spaced inwardly from a peripheral edge 107 of the main absorbent body 11 of the napkin 10d. Preferably the embossed ring 106 is spaced inwardly from the peripheral edge 107 of the main absorbent body 11 by a distance of about 5 mm to about 60 mm.

Figure 15:
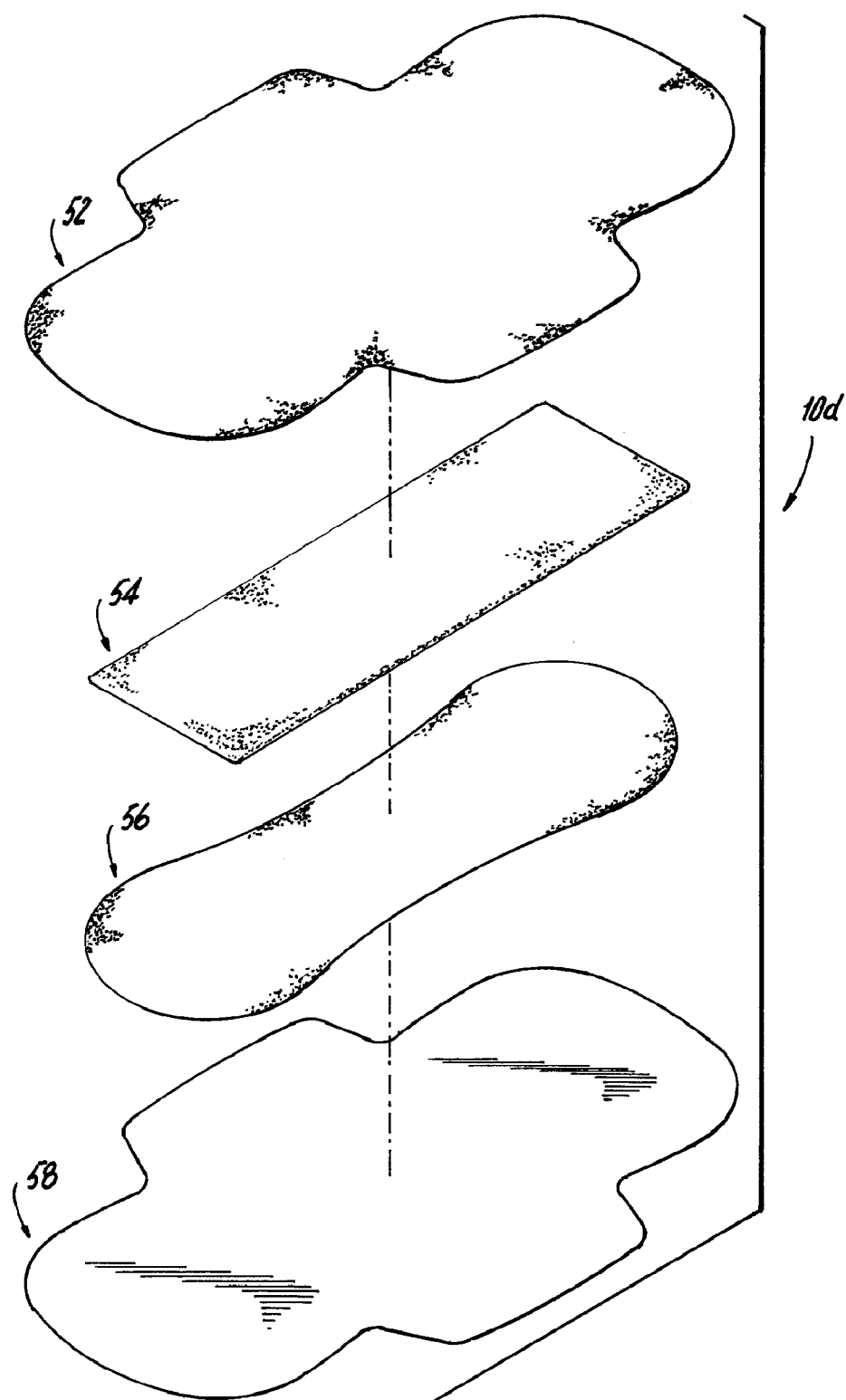
FIG. 15 is an exploded view of the absorbent shown in FIG. 12, depicting the constituent material layers thereof prior to embossing.

In one embodiment of the sanitary napkin 10d shown in FIG. 15, the sanitary napkin 10d includes a fluid permeable cover layer 52, a first absorbent layer 54, a second absorbent layer 56, and a fluid impermeable barrier layer 58. In the embodiment of the invention shown in FIG. 15 the first absorbent layer 54 does not include any material free zones 60 as described above with respect to the first embodiment 10 of the invention. However, the sanitary napkin 10d could be constructed with such material free zones 60 if desired.

Figure 13:
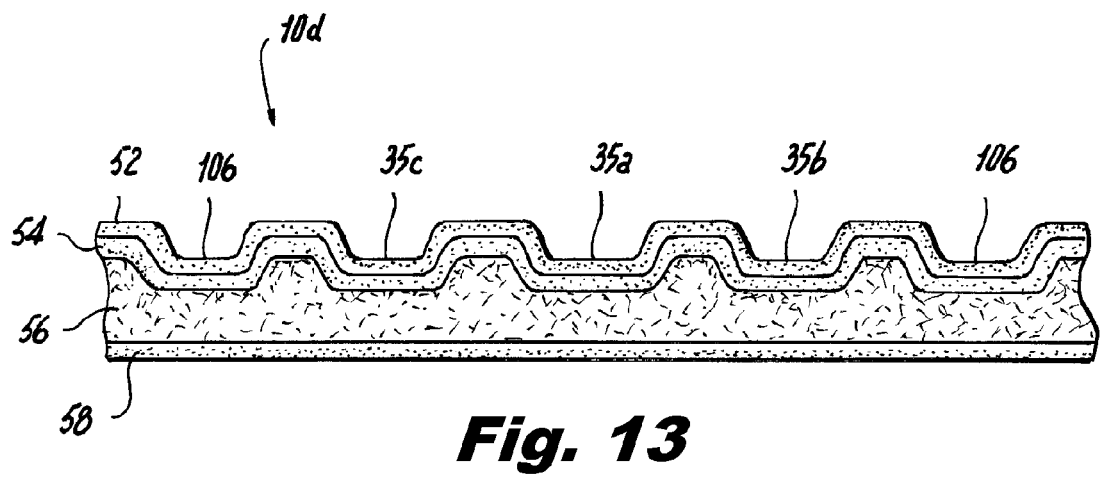
FIG. 13 is a sectional view of the absorbent article shown in FIG. 12 taken along line 13-13 thereof.

Referring to FIGS. 13 and 14, the first embossing pattern 94 and second embossing pattern 32 are structured and arranged such that the embossed regions thereof, i.e. channels 100, embossed ring 106, and channels 35a, 35b and 35c, are formed such that they extend into cover layer 52, first absorbent layer 54 and second absorbent layer 56.

Cover Layer

The cover layer 52 may be a relatively low density, bulky, high-loft non-woven web material. The cover layer 52 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 52 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer and/or to the barrier layer.

The cover layer 52 preferably has a relatively high degree of wettability, although the individual fibers comprising the cover may not be particularly hydrophilic. The cover material should also contain a great number of relatively large pores. This is because the cover layer 52 is intended to take-up body fluid rapidly and transport it away from the body and the point of deposition. Therefore, the cover layer contributes little to the time taken for the napkin to absorb a given quantity of liquid (penetration time).

Advantageously, the fibers which make up the cover layer 52 should not lose their physical properties when they are wetted, in other words they should not collapse or lose their resiliency when subjected to water or body fluid. The cover layer 52 may be treated to allow fluid to pass through it readily. The cover layer 52 also functions to transfer the fluid quickly to the underlying layers of the napkin. Thus, the cover layer 52 is advantageously wettable, hydrophilic and porous. When composed of synthetic hydrophobic fibers such as polyester or bi-component fibers, the cover layer 52 may be treated with a surfactant to impart the desired degree of wettability.

Alternatively, the cover layer 52 can also be made of polymer film having large pores. Because of such high porosity, the film accomplishes the function of quickly transferring body fluid to the inner layers of the underlying absorbent layers.

The cover layer 52 may be attached to the underlying absorbent layers 54 and 56, and/or the barrier layer 58, by adhesion and/or other suitable means know to those of skill in the art.

One material particularly suitable for use as the cover layer 52 is a 27 gsm hot through air (HTA) bonded material commercially available from Shalag Nonwovens Ltd., Upper Galilee, Israel, under product code HTA STA5ETW27.

First Absorbent Layer

The first absorbent layer 54 may be composed of fibrous materials, such as wood pulp, polyester, rayon, flexible foam, or the like, or combinations thereof. The first absorbent layer 54 may also optionally include a superabsorbent polymer (SAP) material. The first absorbent layer 54 may also comprise thermoplastic fibers for the purpose of stabilizing the layer and maintaining its structural integrity. The first absorbent layer 54 may be treated with surfactant on one or both sides in order to increase its wettability, although generally the first absorbent layer 54 is relatively hydrophilic and may not require treatment. The first absorbent layer 54 is preferably bonded on both sides to the adjacent layers, i.e. the cover layer 52 and the underlying second absorbent layer 56.

In specific embodiments of the present invention the first absorbent layer 54 may be a "transfer" layer. The transfer layer provides means for receiving body fluid from the fluid-pervious cover layer 52 and holding it until the second absorbent layer 54 has an opportunity to absorb it. The transfer layer is, preferably, more dense than the fluid-pervious cover layer 52 and has a larger proportion of smaller pores than does the latter. These attributes allow the transfer layer to contain body fluid and hold it away from the outer side of the fluid-pervious cover layer 52, thereby preventing the fluid from re-wetting the fluid-pervious cover layer 54 and its surface. However, the transfer layer is preferably not so dense as to prevent the passage of the fluid through the transfer layer and into the underlying second absorbent layer 54.

When constructed as a transfer layer, the first absorbent layer 52 may comprise various materials, including, for example, cellulose fibers such as from wood pulp, single component or bicomponent fibers that include thermoplastic materials (such as polyester, polypropylene, polyethylene, among others) in fiber or other forms, rayon, organic binders (such as copolymers of vinyl, acrylic and/or other monomers that may be coated onto thermoplastic fibers or otherwise incorporated into the transfer layer) among other materials known to the art.

One material particularly useful as the first absorbent layer 52 is a 90 gsm airlaid material including pulp fibers, bi-component fibers, and a synthetic binder commercially available from Glatfelter Gatineau Ltd., Gatineau, Canada under product code MH090.102.

Second Absorbent Layer

The second absorbent layer 56 may comprise a single layer of material or may comprise multiple layers. In preferred embodiments of the present invention the second absorbent layer 56 functions as the absorbent core of the sanitary napkin 10. In preferred embodiments of the present invention the second absorbent layer 56 functions as an absorbent core. Preferably, such absorbent core has a high total absorbent capacity and function to hold fluid upon receiving such fluid from the transfer layer. In addition, the absorbent core preferably has a greater density than that of the transfer layer.

In one embodiment, the second absorbent layer 56 is a blend or mixture of cellulosic fibers and superabsorbent disposed therein. Cellulosic fibers that can be used in the second absorbent layer 56 are well known in the art and include wood pulp, cotton, flax and peat moss. Wood pulp is preferred.

Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material. Some portion of the pulp may be chemically treated as discussed in U.S. Pat. No. 5,916,670 to improved flexibility of the product. Flexibility of the material may also be improved by mechanically working the material or tenderizing the material.

The second absorbent layer 56 can contain any superabsorbent polymer (SAP) which are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA70N and products offered by Stockhausen Inc. In a specific example, the second absorbent layer 56 is a material containing from 90% to about 40% percent cellulosic fiber, about 10% to about 60% SAP. The second absorbent layer 56 may comprise a material manufactured by using air-laying means well known in the art.

Another material useful at the second absorbent layer 56, particularly in the embodiment of the invention shown in FIGS. 12-15, is a pin-embossed material formed from wood pulp and superabsorbent polymer of the type described in U.S. patent application Ser. No. 12/855,070.

Barrier Layer

Underlying the second absorbent layer 56 is a barrier layer 58 comprising liquid-impervious film material so as to prevent liquid that is entrapped in the absorbent layer 56 from egressing the sanitary napkin and staining the wearer's undergarment. The barrier layer 58 is preferably made of polymeric film, although it may be made of liquid impervious, air-permeable material such as repellent-treated non-woven or micropore films or foams.

The barrier layer 58 may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 52 and the barrier layer 58 are preferably joined along their marginal portions so as to form an enclosure or flange seal that maintains the absorbent layers 54 and 56 captive. The joint may be made by means of adhesives, heat-bonding, ultrasonic bonding, radio frequency sealing, mechanical crimping, and the like and combinations thereof.

Positioning adhesive may be applied to a garment facing surface of the barrier layer 58 for securing the napkin 10 to a garment during use. The positioning adhesive may be covered with removable release paper so that the positioning adhesive is covered by the removable release paper prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety. As disclosed in the above documents, wings are generally speaking flexible and configured to be folded over the edges of the underwear so that the wings are disposed between the edges of the underwear.

As illustrated by the above description and the accompanying drawings absorbent articles according to the present invention provide a structure that enables such article to provide superior wicking characteristics while at the same time providing superior fluid penetration characteristics.

We claim:

1. An absorbent article, comprising:
a longitudinally extending centerline;
a transversely extending centerline;
a first end region and a second end region;
a central region arranged between the first and second end regions;
a first longitudinal edge;
a second longitudinal edge;
a first transverse edge;
a second transverse edge;
a main absorbent body;
a first embossing pattern having a first portion arranged in the first end region and a second portion arranged in the second end region, each of the first and second portions including a plurality of interconnected channels, the interconnected channels defining a plurality of body facing protrusions;
a second embossing pattern in the central region including at least one channel extending in a longitudinal direction of the article provided that the channels extending in the longitudinal direction in the second embossing pattern are in a spaced relationship, the at least one channel intersecting at least one of the plurality of interconnected channels in the first end region and at least one of the plurality of interconnected channels in the second end region,
wherein said second embossing pattern in the central region is different from the first embossing pattern at least one of the first end region or the second end region.

2. The absorbent article according to claim 1, wherein an apex of each of the protrusions extends about 1 mm to about 10 mm above a base surface of a surrounding interconnected channel.

3. The absorbent article according to claim 2, wherein each protrusion is substantially surrounded by at least one of the interconnected channels.

4. The absorbent article according to claim 3, wherein the plurality of interconnected channels define a continuous network of channels.

5. The absorbent article according to claim 4, wherein the at least one longitudinally extending channel comprises a plurality of longitudinally extending channels, one of the longitudinally extending channels extending with the longitudinally extending centerline of the article, and the other longitudinally extending channels being arranged in spaced relationship to the channel that is extending with the longitudinally extending centerline.

6. The absorbent article according to claim 5, wherein the longitudinally extending channel extending with the longitudinally extending centerline intersects at least one of the plurality of channels in the first end region and at least one of the plurality of channels in the second end region.

7. The absorbent article according to claim 6, wherein each one of the plurality of longitudinally extending channels is a continuous channel.

8. The absorbent article according to claim 7, wherein the first portion is arranged in spaced relationship to the second portion.

9. The absorbent article according to claim 8, further comprising an embossed ring.

10. The absorbent article according to claim 9, wherein the embossed ring is spaced outwardly relative to first and second embossing patterns.

11. The absorbent article according to claim 10, wherein the embossed ring is structured and arranged such that first and second end regions of the embossed ring are spaced further from the first and second embossing patterns than a first and second side region of the embossed ring.

12. The absorbent article according to claim 11, wherein the embossed ring is spaced inwardly relative to a peripheral edge of the main absorbent body.

13. The absorbent article of claim 1, wherein the at least one channel extending in the longitudinal direction in the second embossing pattern is in a spaced relationship from the other channels such that the at least one channel does not intersect the longitudinally extending centerline of the absorbent article.

14. The absorbent article of claim 1, wherein said at least two channels are in a spaced relationship such that they do not intersect the longitudinally extending centerline of the absorbent article.

15. The absorbent article of claim 1, wherein said at least two channels are symmetric about the longitudinally extending centerline.

16. An absorbent article, comprising:
- a longitudinally extending centerline;
- a transversely extending centerline;
- a first end region and a second end region;
- a central region arranged between the first and second end regions;
- a first longitudinal edge;
- a second longitudinal edge;
- a first transverse edge;
- a second transverse edge;
- a main absorbent body;
- a first embossing pattern having a first portion arranged in the first end region and a second portion arranged in the second end region, each of the first and second portions including a plurality of interconnected channels, the interconnected channels defining a plurality of body facing protrusions;
- a second embossing pattern in the central region including at least two channels extending in a longitudinal direction of the article provided that the channels extending in the longitudinal direction in the second embossing pattern are in a spaced relationship, wherein at least one channel intersects at least one of the plurality of interconnected channels in the first end region and at least one of the plurality of interconnected channels in the second end region, wherein said second embossing pattern in the central region is different from the first embossing pattern at least one of the first end region or the second end region.

17. An absorbent article, comprising:
- a longitudinally extending centerline;
- a transversely extending centerline;
- a first end region and a second end region;
- a central region arranged between the first and second end regions;
- a first longitudinal edge;
- a second longitudinal edge;
- a first transverse edge;
- a second transverse edge;
- a main absorbent body;
- a first embossing pattern having a first portion arranged in the first end region and a second portion arranged in the second end region, each of the first and second portions including a plurality of interconnected channels, the interconnected channels defining a plurality of body facing protrusions;
- a second embossing pattern in the central region including at least one channel extending in a longitudinal direction of the article provided that the channels extending in the longitudinal direction in the second embossing pattern are in a spaced relationship, the at least one channel intersecting at least one of the plurality of interconnected channels in the first end region and at least one of the plurality of interconnected channels in the second end region,
- wherein said second embossing pattern in the central region is different from the first embossing pattern at least one of the first end region or the second end region; and
- wherein said pad comprises a cover layer and a first absorbent layer, wherein the first absorbent layer comprises at least one material free zone that provides for the least one channel of the second embossing pattern.

18. The absorbent article of claim 17, further comprising a second absorbent layer.

19. The absorbent article of claim 18, wherein the cover layer contacts the second absorbent layer through the at least one material free zone.

20. The absorbent article of claim 17, wherein the at least one channel extending in the longitudinal direction in the second embossing pattern is in a spaced relationship from the other channels such that the at least one channel does not intersect the longitudinally extending centerline of the absorbent article.

\* \* \* \* \*